United States Patent [19]

Lang et al.

[11] 4,083,979
[45] Apr. 11, 1978

[54] THIAZOLIDINE DERIVATIVES AND THEIR USE AS SALIDIURETICS

[75] Inventors: Hans-Jochen Lang, Altenhain, Taunus; Roman Muschaweck, Frankfurt am Main, both of Germany

[73] Assignee: Hoechst Aktiengesellschaft, Frankfurt am Main, Germany

[21] Appl. No.: 732,135

[22] Filed: Oct. 13, 1976

[30] Foreign Application Priority Data

Oct. 15, 1975 Germany .............................. 2546165

[51] Int. Cl.² .................. C07D 277/18; A61K 31/425
[52] U.S. Cl. .............................. 424/251; 260/256.5 R; 260/293.57; 260/293.68; 260/306.7 T; 260/566 C; 424/267; 424/270; 548/324
[58] Field of Search ................ 260/306.7 T, 256.5 R, 260/293.57, 293.68, 309.6, 556 C; 424/270, 251, 267

[56] References Cited

FOREIGN PATENT DOCUMENTS

1,365,977   9/1974   United Kingdom .......... 260/306.7 T

*Primary Examiner*—Richard J. Gallagher
*Attorney, Agent, or Firm*—Curtis, Morris & Safford

[57] ABSTRACT

Diuretically active thiazolidine compounds and methods for making the same are disclosed, said compounds having an alkyl or alkenyl substituent in the 1-position, an imino group in the 2-position, and an hydroxy group and an N-acylated 3'-sulfamoylphenyl substituent in the 4-position, i.e.

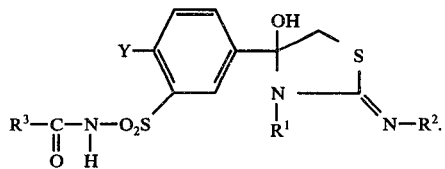

8 Claims, No Drawings

THIAZOLIDINE DERIVATIVES AND THEIR USE AS SALIDIURETICS

The present invention relates to thiazolidine derivatives of the general formula I

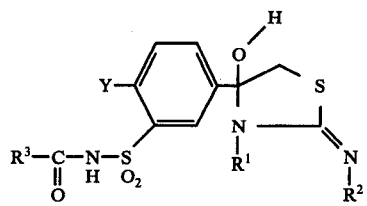
(I)

in which $R^1$ represents alkyl or alkenyl radicals of 1 to 4 carbon atoms, $R^2$ represents an alkyl or alkenyl group of 1 to 6 carbon atoms which may be substituted by alkoxy groups of 1 to 2 carbon atoms, cycloalkyl groups of 3 to 8 carbon atoms, phenylalkyl groups of 1 to 2 carbon atoms in the alkyl moiety, and in which $R^1$ and $R^2$ together may represent an alkylene chain of 2 to 4 carbon atoms which may be branched, $R^3$ represents hydrogen, lower alkyl or alkoxy of 1-3 carbon atoms or an amino group $-NR^4R^5$, $R^4$ and $R^5$ being identical or different and representing hydrogen, a lower alkyl radical of 1 to 4 carbon atoms or if $R^5$ is hydrogen, $R^4$ represents a cycloalkyl radical of 5 to 8 carbon atoms or $R^4$ in combination with $R^5$ may form together with the N-atom a 5- to 7-membered saturated heterocyclic ring and Y represents chlorine or bromine and to their acid addition salts with physiologically tolerated acids.

The invention furthermore relates to a process for preparing the compounds of the above general formula I, which comprises (a) reacting compounds of the general formula II

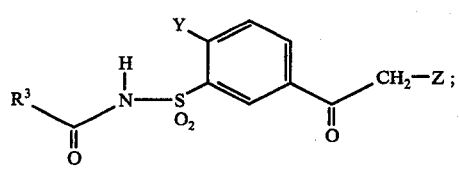
(II)

in which $R^3$ and Y have the meanings given above, and Z represents the radical of an activated ester of a mineral or organic acid, with thio-ureas of the general formula III, which may be present in the form represented by the two formulae IIIa and IIIb

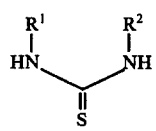

in which $R^1$ and $R^2$ have the meanings given above, or (b) reacting compounds of the general formula IV

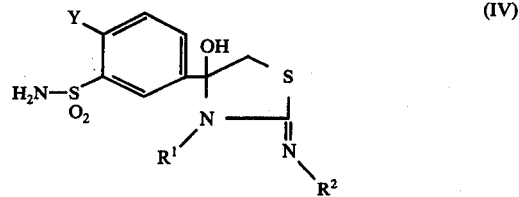
(IV)

their acid addition salts or their metal salts of the general formula V

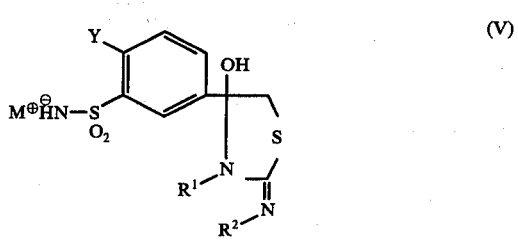
(V)

in which M stands for alkali metal or alkaline earth metal, with a reactive derivative of an acid of the formula $R^3$—COOH, optionally in the presence of a base, or (c) splitting under hydrolysis the 2-halogeno-5-(2-imino-1,3-thiazolidine-4-ol-4-yl)-benzenesulfonyl-isourea ether, or the corresponding isothiourea ether of the general formula VI

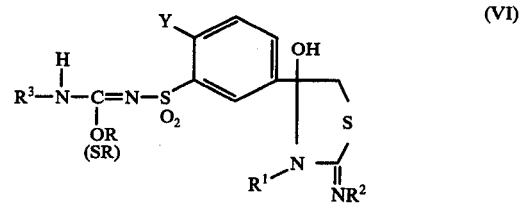
(VI)

in which R stands for alkyl and $R^1$, $R^2$, $R^3$ and Y are defined as above, or (d) reacting compounds of the general formula VII

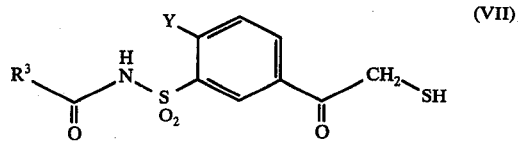
(VII)

with compounds of the formula VIII

(VIII)

in which $R^1$, $R^2$, $R^3$ and Y are defined as above and Hal stands for chlorine or bromine, or (e) reacting compounds of the formula VII with carbodiimides IX $$R^1-N=C=N-R^2 \quad (IX)$$

in which $R^1$ and $R^2$ are defined as above or (f) treating compounds of the general formula X

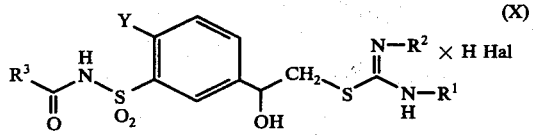

in which $R^1$, $R^2$, $R^3$ and Y are defined as above, and Hal stands for chlorine or bromine, with an oxidizing agent, and, if desired, transforming the compounds of the general formula I obtained according to methods (a) to (f) with organic or mineral acids into their acid addition salts or the salts obtained of the compounds of the general formula I with bases into the free basic compounds of the formula I or into their alkali- or ammonium salts.

Mineral acids which may be used are, for example, hydrohalic acids such as hydrochloric acid and hydrobromic acid, as well as sulfuric acid, phosphoric acid and amino-sulfonic acid.

Organic acids which may be used are, for example, formic acid, acetic acid, benzoic acid, succinic acid, fumaric acid, maleic acid, lactic acid, tartaric acid, citric acid, salicyclic acid, oxyethanesulfonic acid, ethylenediaminetetraacetic acid, methane-sulfonic acid, p-toluenesulfonic acid, etc.

The compounds of the formula I may also be present in their tautomeric forms Ia:

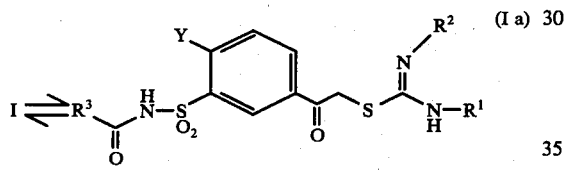

The compounds of the formula I may, in addition, also be present in their possible geometrical isomeric structures.

Via the open-chain tautomeric form Ia, the cyclic compounds of the formula I, with different $R^1$ and $R^2$, are in equilibrium with the position-isomeric compounds of the formula Ic and their acid addition salts

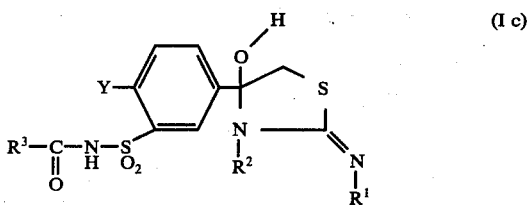

Which of the two cyclic isomers I or Ic or their acid addition salts are present to a preponderant degree depends essentially on the different spatial filling of the substituents $R^1$ or $R^2$ in that the spatially smaller substituent fixes preferably in the position 3 of the thiazolidine ring system. For the sake of simplicity, only one of the possible isomeric or tautomeric forms of a substance is indicated for the compounds of the invention.

Method (a) is carried out advantageously by reacting the compounds of the formula II with the thio-ureas of the formula III in a molar ratio of 1:1 to 1:1.5. Higher molar excess amounts of thio-ureas generally do not give significant advantages. The reaction is advantageously carried out in an inert solvent, for example in polar organic solvents such as dimethyl formamide, dimethylacetamide, dioxane, tetrahydrofurane, acetonitrile, nitromethane, diethylene-glycol-dimethyl ether, etc. Acetic acid, lower alkyl esters such as methyl acetate and ethyl acetate, lower alcohols containing 1 to 4 carbon atoms, in particular methanol, ethanol, and isopropanol, and lower dialkyl ketones, for example acetone and methyl-ethyl ketone proved particularly advantageous reaction media. Mixtures of the mentioned solvents may also be used as well as mixtures of the mentioned solvents with less appropriate solvents, for example methanol/benzene, ethanol/toluene, methanol/diethyl ether, ethanol/carbon tetrachloride, acetone/chloroform, it being of advantage that the solvent with a higher polarity be present in an excess amount. The reaction partners may be present in the respective solvent in suspended or dissolved form. Principally, the reaction partners may also be reacted without using a solvent, in particular in those cases where the respective thiourea has a very low melting point, but in these cases side-reactions may occur by reason of the exothermic reaction course so that this process variant does not bring any advantages over the method of operation in solvents. The reaction proceeds moderately exothermically and can be carried out at between 0° and 100° C, preferably at between 10° and 70° C. A temperature range from 20° to 55° C, proved particularly advantageous.

The reaction time depends largely on the reaction temperature and is between 2 minutes in the higher temperature ranges and 60 hours at lower temperature. In the favorable temperature range, the reaction time is generally between 5 minutes and 40 hours.

In many cases the compounds I in the form of their acid addition salts, separate during the reaction in a sparingly soluble form, in which case the yield may be increased optionally by subsequent addition of a suitable precipitant. As precipitants, there may be used, for example, hydrocarbons such as benzene, toluene, cyclohexane, petroleum ether, or ligroin, carbon tetrachloacetic acid lower alkyl esters containing 1 to 4 carbon atoms in the alkyl moiety, such as ethyl acetate and n-butyl-acetate, and dialkyl ethers containing 4 to 8 carbon atoms, such as diethyl ether, diisopropyl ether and di-n-butyl ether, proved especially appropriate. If, after termination of the reaction, a solution is obtained, the salts of the compounds of the formula I are precipitated with one of the aforementioned precipitants, optionally after previous concentration of the reaction solution, or, advantageously, in order to remove inhomogeneous impurities, the solution is filtered into one of the mentioned precipitants, while stirring. Since the reaction of the compounds II with the thio-ureas III, if effected under optimum conditions, practically proceeds quantitatively, the crude products so obtained of the desired compounds are in most cases already analytically pure.

The thio-ureas III used are in most cases substances which are described in the literature. They are obtained in known manner by the reaction of amines with isothio-cyanates, carbon disulfide or thiophosgene (cf. Houben-Weyl, "Methoden der organischen Chemie", Vol. 9, page 884, 4th Edition, Stuttgart, 1955).

In the compounds of the formula II, there may be used as the radical of an activated ester Z, for example Cl, Br, I, $CH_3$—$SO_2$—O—, $C_2H_5$—$SO_2$—O—, $C_6H_5$—$SO_2$—O— and $CH_3C_6H_4$—$SO_2$—O—. They can be obtained by several methods known per se.

A preferred method of preparing the compounds of the general formula II in which $R^3$ and Y are defined as above, and Z stands for chlorine or bromine, is the reaction of compounds of the general formula XI

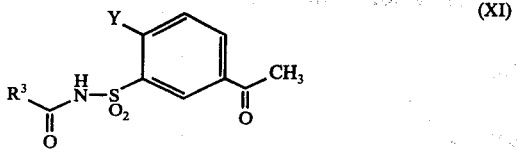

with a halogenating agent, for example with elementary chlorine or bromine, sulfuryl chloride, mono-chlorourea, copper-II-bromide, bromodioxane, or N-bromosuccinimide under known conditions, or the acylation of the sulfamoyl group in α-halogeno-ketones of the general formula XII

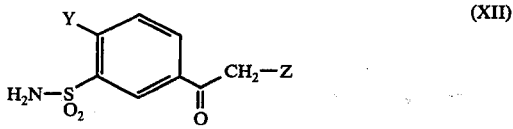

with an activated derivative of an acid of the formula $R^3$—$CO_2H$ indicated in the operational method (b) in a manner known in the literature. Compounds of the formula II, in which Z is not halogen, but another radical of an activated ester, can be obtained, for example, by reacting α-hydroxy-ketones of the formula XIII

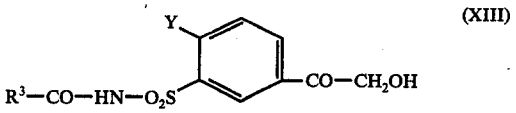

with the activated derivatives of organic and mineral acids such as methane-sulfonic acid chloride, ethane-sulfonic acid chloride, benzene-sulfonic acid chloride, p-toluene-sulfonic acid chloride, thionyl chloride, phosphorus trichloride, phosphorus tribromide, phosphorus oxide chloride, or p-nitrobenzoyl chloride under conditions known in the literature. The intermediate products of the general formula XI can be obtained according to methods disclosed in the literature and in a manner analogous to the operational method (b) or (c) from 2-halogeno-5-acetyl-benzene-sulfonyl amide (cf. Arzneimittelforschung, 13, 269 (1963)).

According to the operational method (b) the sulfamoylthiazolidines of the general formula IV are reacted with one of the above-mentioned reactive derivatives of an acid of the formula $R^3$—$CO_2H$, such as acyl halides and anhydrides, acyl-1-imidazoles, isocyanates, carbamic acid halides, advantageously in the presence of a base. Since the preferred acylating agents are acid chlorides, carboxylic acid anhydrides and alkyl isocyanates, which are liquid at room temperature, the reaction can be carried out in the pure acylating agent. But the reaction is preferably carried out in a polar organic solvent, for example dimethyl sulfoxide, dimethylformamide, diethylene glycol dimethyl ether, acetonitrile, acetone, ethyl acetate, tetrahydrofuran, dioxan, the reactions with isocyanates being carried out in addition to the solvents mentioned also, for example, in lower alcohols, such as methanol, ethanol, isopropanol, n-butanol or the mixtures thereof with water.

To carry out the acylation reactions as specifically as possible on the sulfonamido group under mild conditions, it is advantageous to use a base, for example hydroxides, methylates, ethylates, isopropylates, tertiary butylates, carbonates, methylsulfonyl methides of the alkali metals or alkaline earth metals. It is known that these bases deprotonize the sulfonamido group and convert the compound IV before its acylation into the salts of the general formula V which are then reacted with the acylation agent. The salts V are preferably prepared in the reaction medium immediately before the acylation step and further reacted without isolation.

Temperatures within the range of from $-30°$ to $+60°$ C, preferably $0°$ to $+30°$ C, advantageously $18°$ to $25°$ C are suitable.

Principally, the salts of the formula V can also be isolated and then reacted with one of the above-mentioned acylation agents. The preparation and isolation of the compounds of the formula V are advantageously carried out in such a manner that 1 to 1.2 mols of base, for example KOH or $NaOCH_3$ are added to the thiazolidines of the formula IV in a suitable solvent, for example in water or in methanol and the aqueous solution is lyophilized or evaporated at temperatures below $+40°$ C under reduced pressure or the salts are precipitated from the organic medium with a suitable precipitating agent, for example diethyl ether, diisopropyl ether, benzene, toluene, petroleum ether, ethyl acetate, isopropyl acetate, acetone or mixtures of the solvents indicated above.

The liquid acylation agent is allowed to act on the isolated compounds of the general formula V, that is added dropwise in pure state or in the form of a solution, preferably in one of the solvents named as reaction medium. The respective acylation agent is allowed to act over a period of from 6 hours to 5 days at a temperature within the range of from $-10°$ to $+45°$ C, preferably between $+15°$ and $+30°$ C and the course of the reaction is observed in the thin-layer chromatogram on silica gel using methanol, ethanol, or a mixture of methanol and benzene (in the ratio of 5:1) as eluant. In the aftertreatment, gaseous HBr or HCl is introduced until the reaction occurs in the acid range, the reaction mixture is condensed under reduced pressure and at a bath temperature below $55°$ C and the residue is preferably digested in methanol, ethanol or isopropanol. The inorganic salt is separated by filtration or centrifugation and the desired thiazolidine I is obtained in the form of an acid addition salt after evaporating the solvent or by precipitation with one of the precipitating agents described under method (a). Suitable carbamic acid halides are above all the chlorides.

The benzenesulfonyl-isourea ethers and -isothiourea ethers named as starting substances in method (c) ar split advantageously by alkaline hydrolysis. Isourea ethers may also be split in an acid medium.

The benzenesulfonyl-isourea ethers are prepared according to methods disclosed in the literature. For example, a 4-halogeno-3sulfamoylacetophenone is converted with an alkyl isothiocyanate into a 2-halogeno-5-acetyl-benzenesulfonyl thiourea. The latter can be transformed, for example by the action of phosgene and subsequent reaction with an alcohol, into a 2-halogeno-5-acetylbenzenesulfonyl isourea which is halogenated according to method (a) and finally reacted with a thiourea of the formula III. When dicyclohexyl carbodiimide is used instead of phosgene, a 2-halogeno-5-acetyl-benzenesulfonyl carbodiimide is obtained that yields, on reaction with an alcohol, the 2-halogeno-5-acetyl-benzenesulfonyl-isourea just described. The operational methods described are illustrated in the following scheme:

According to method (d), compounds of the formula VII are reacted in a solvent with the known compounds of the formula VIII. Suitable solvents are lower alcohols of 1 to 4 carbon atoms as well as lower alkyl esters of acetic acid having 1 to 4 carbon atoms in the alkyl moiety, for example methyl acetate and ethyl acetate.

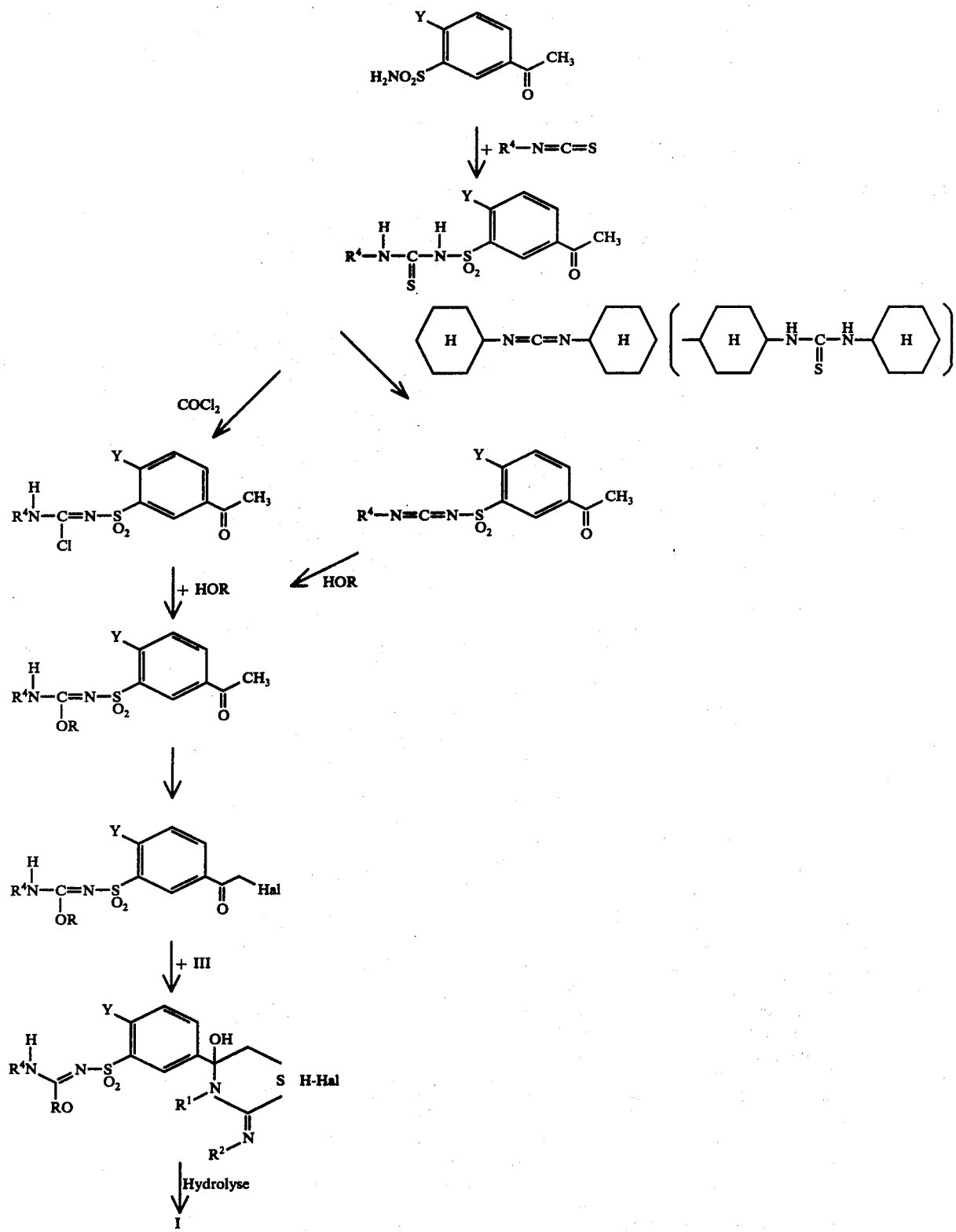

The reactions are carried out generally at a temperature within the range of from 0° to 60° C, preferably 15° to 35° C, and within a reaction time of from 5 to 60 hours.

For carrying out the method (e), the mercapto-ketones of the formula VII are reacted in an anhydrous polar inert solvent, for example in dioxane, tetrahydrofuran, methyl acetate or ethyl acetate, with the carbodiimides of the formula IX in a molar ratio of 1:1. The reactions can be carried out in a temperature range of from 0° to 40° C, preferably from 10° to 30° C, the reaction time being between 1 and 20 hours.

The compounds of the formula IX are known or are prepared in a manner analogous to the known methods.

The compounds of the formula VII used in the methods (d) and (e) may be prepared in various ways. For example, the compounds of the formula II can be converted with thiocarboxylic acids of the formula XIII

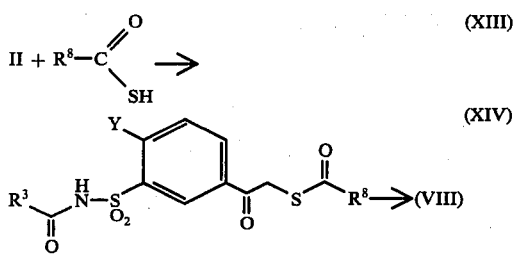

preferably with thio-acetic acid ($R^8$=$CH_3$) in the presence of two equivalent bases, for example KOH, in an aqueous or alcoholic medium into the thio-esters of the general formula XIV which are hydrolyzed in a weakly alkaline medium to the compounds of the formula VII.

Another possibility consists in the reaction of the compounds of the formula VII with alkali metal hydrogen sulfides such as sodium or potassium hydrogen sulfide in an inert solvent such as dimethylformamide at temperatures between 0° and 40° C.

According to method (f), the compounds of the general formula X are converted with the aid of a suitable oxidizing agent, preferably with active manganese-IV oxide, into the compounds of the formula I or their acid addition salts. As solvents, preferably halogenated hydrocarbons such as methylene chloride, chloroform, or tetrachloroethane are used and the reaction is carried out at temperatures in the range of from 0° to 40° C, preferably from 20° to 30° C, over a period of time of 10 to 60 hours.

The compounds of the formula X are obtained by converting the halogenoketones of the formula II, in which Z preferably represents chlorine or bromine, for example according to the method described in Arzneimittelforschung 22, 2095 (1972), with a suitable reducing agent, preferably with sodium boronhydride in methanol at temperatures between 0° and 25° C into compounds of the formula XV

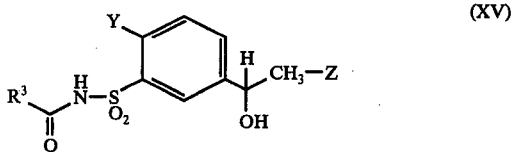

As alkyl-halides, the compounds of the formula XV react with the thio-ureas of the formula III to give the iso-thio-uronium salts of the formula X. The reaction conditions correspond to those indicated for method (a).

The compounds of the formulae I and V can be reacted in reversible manner in a suitable solvent with an acid of the formula H—Z. The compounds I or V can be introduced into the pure acids at temperatures in the range of from 0° to 40° C, provided that these acids are liquid or have a melting point which is not essentially higher than 40° C. It is, however, advantageous to work in a solvent, for example in water, or in an organic solvent, for example in dioxane, tetrahydrofurane, ether, an acetic lower alkyl ester containing 1 to 4 carbon atoms in the alkyl moiety, acetonitrile, nitromethane, acetone, methyl-ethyl ketone, etc., lower alcohols containing 1 to 4 carbon atoms being especially suitable. Per mole of the compound I, 1 to 1.5 moles and per mole of the compound V 2-2.5 moles of the acids are used, it being also possible to use higher amounts of acid. It is suitable to operate at temperatures between 0° and 40° C, preferably between 10° and 25° C. The reaction is moderately exothermic. When working in an aqueous solution, the compounds I dissolve immediately after addition of the acids H—Z and in rare cases the corresponding acid addition salts are precipitated. When a solution is obtained, the salts of the invention are isolated by mild evaporation of the water, preferably by lyophilization. When working in organic solvents, the acid addition salts often precipitate in a sparingly soluble form after addition of the respective acid H—Z. If a solution is obtained, the acid addition salts are precipitated with the aid of a suitable precipitant, optionally after previous concentration. As precipitants, there are suitable the solvents described for the same purpose under method (a).

The acid addition salts are often obtained in the form of viscous oils or amorphous glass-like products, even upon thorough purification. These amorphous products can be brought to crystallization in many cases optionally by heating to 40° to 80° C while treating with an organic solvent. Solvents which promote the crystallization are in particular acetic acid lower alkyl esters having 1 to 4 carbon atoms in the alkyl moiety, for example methyl acetate, ethyl acetate, n-butyl acetate, lower dialkyl ketones such as acetone or methylethyl ketone, lower dialkyl ethers such as diethyl ether, dieisopropyl ether or di-n-butyl ether, as well as acetonitrile, nitromethane, and in some cases also lower alcohols such as methanol, ethanol, isopropanol or n-butanol.

The acid addition products can be deprotonized to compounds of the general formula I by treatment with bases in a suitable solvent. As bases, there may be used, for example solutions of mineral hydroxides such as the hydroxides of lithium, sodium, potassium, calcium or barium, carbonates or bicarbonates such as sodium carbonate, potassium carbonate, sodium bicarbonate or potassium bicarbonate, ammonia and amines, for example triethylamine, dicyclohexylamine, piperidine, methyl-dicyclohexylamine.

When an excess base is added, the compounds I are easily converted with further deprotonization of the acylsulfamoyl group, into the salts of the formula XVI

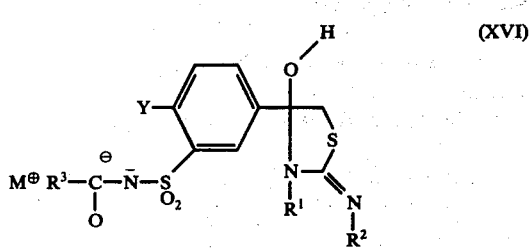

(XVI)

in which $R_1$ to $R^3$, Y and M are defined as above, and the preparation of the amphoteric compounds I of the invention must be carried out in a narrow pH range, which is between 4 and 6, depending on the nature of the substituents $R^1$ to $R^3$, and is evaluated by drawing a titration curve.

When working in an aqueous medium, the free basic compounds of the formula I precipitate in a sparingly soluble form and can be separated and isolated by filtration or extraction with an organic solvent, preferably with ethyl acetate. Suitable organic reaction media are in particular lower alcohols containing 1 to 4 carbon atoms, preferably methanol and ethanol, but ethyl acetate, diethyl ether, tetrahydrofurane, dioxane, diethyl glycol dimethyl ether, dimethylformamide, etc. may also be used. The reaction to the compounds I takes place spontaneously. The reaction is carried out at a temperature in the range of from $-35°$ to $100°$ C, preferably from $0°$ to $25°$ C. If a water-miscible organic solvent is used, the free bases of the formula I are precipitated by the addition of water, optionally after previous concentration of the reaction mixture. If a solvent which is not miscible with water is used, it is advantageous to wash the reaction mixture with water after completion of the reaction and to evaporate the organic solvent, optionally after previous drying.

Among the compounds of the invention of the formula I and their pharmacologically tolerated salts, in particular those are of interest in which $R^1$ represents methyl, ethyl or allyl, $R^2$ represents an alkyl or alkenyl radical containing 1 to 4 carbon atoms and which may be substituted by a methoxy or ethoxy group, cycloalkyl radicals and phenyl alkyl radicals as defined above and in which $R^1$ and $R^2$ may also represent together an alkenyl chain of 2 to 4 carbon atoms, Y represents chlorine or bromine and $R^3$ represents methyl or $-NR^4R^5$ in the meaning given above.

In addition to the 4-(3-sulfamoyl-phenyl)-1,3-thiazolidine-4-ols described in the Examples, there may also be prepared according to the invention, for example the compounds of the formula I listed in the following Tables

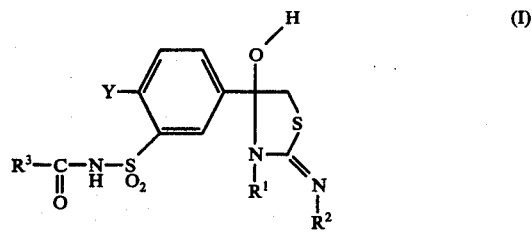

(I)

and their acid addition salts.

| | $R^1$ | $R^2$ | $R^3$ | Y |
|---|---|---|---|---|
| 1 | $C_2H_5$ | ![cyclopentyl] | $CH_3$ | Cl |
| 2 | $CH_3$ | $-CH_2-CH(OCH_3)-CH_3$ | $CH_3$ | Cl |
| 3 | $C_2H_5$ | $-(CH_2)_2-OCH_3$ | $CH_3$ | Cl |
| 4 | $C_2H_5$ | $CH_2-CH(CH_3)_2$ | $OCH_3$ | Cl |
| 5 | $C_2H_5$ | cyclohexyl-H | $OCH_3$ | Cl |
| 6 | $CH_3$ | $-CH_2-CH(OCH_3)-CH_3$ | $OCH_3$ | Cl |
| 7 | $CH_3$ | $-(CH_2)_2$-phenyl | $OCH_3$ | Cl |
| 8 | $CH_2=CH-CH_2$ | $CH_2=CH-CH_2-$ | $OCH_3$ | Cl |
| 9 | $CH_3$ | $-CH(CH_3)-CH_2-CH_3$ | $C_2H_5$ | Cl |
| 10 | $CH_3$ | cyclohexyl-H | $C_2H_5$ | Cl |
| 11 | $CH_3$ | $CH_3$ | $-CH(CH_3)_2$ | Cl |

-continued

| | R¹ | R² | R³ | Y |
|---|---|---|---|---|
| 12 | CH₃ | -CH₂-CH(CH₃)CH₃ | -CH(CH₃)CH₃ | Cl |
| 13 | CH₂=CH-CH₂- | CH₂=CH-CH₂- | -CH(CH₃)CH₃ | Cl |
| 14 | CH₃ | -CH₂-C₆H₅ | -CH(CH₃)CH₃ | Cl |
| 15 | CH₃ | -CH₂-CH(OCH₃)-CH₃ | OC₂H₅ | Cl |
| 16 | C₂H₅ | -C₆H₁₁ (cyclohexyl) | OC₂H₅ | Cl |
| 17 | CH₃ | -CH₂-C₆H₅ | OC₂H₅ | Cl |
| 18 | CH₃ | -CH(CH₃)-CH₂CH₃ | OC₂H₅ | Br |
| 19 | CH₃ | CH₃ | NH₂ | Cl |
| 20 | C₂H₅ | -CH(CH₃)CH₃ (isopropyl) | NH₂ | Cl |
| 21 | CH₂=CH-CH₂ | CH=CH-CH₂ | NH₂ | Cl |
| 22 | CH₃ | cyclopentyl | NH₂ | Cl |
| 23 | CH₃- | -(CH₂)₂-C₆H₅ | NH₂ | Cl |
| 24 | | -(CH₂)₂- | NH₂ | Cl |
| 25 | C₂H₅ | -C₆H₁₁ (cyclohexyl) | NH-CH₃ | Cl |
| 26 | C₂H₅ | -CH₂-C₆H₅ | NH-CH₃ | Cl |
| 27 | | -(CH₂)₂- | NH-CH₃ | Cl |
| 28 | | -(CH₂)₃- | NH-CH₃ | Cl |
| 29 | CH₃ | CH₃ | NH-CH₃ | Br |
| 30 | CH₃ | -CH(CH₃)CH₃ | NH-CH₃ | Br |
| 31 | CH₃ | -C₆H₁₁ (cyclohexyl) | NH-CH₃ | Br |
| 32 | CH₃ | -CH₂-CH(OCH₃)-CH₃ | NH-CH₃ | Br |
| 33 | CH₃ | -CH₂-CH=CH₂ | NH-CH₃ | Br |
| 34 | CH₃ | -CH₂-C₆H₅ | NH-CH₃ | Br |
| 35 | CH₃ | CH₃ | NH-CH(CH₃)CH₃ | Cl |

-continued

| | R¹ | R² | R³ | Y |
|---|---|---|---|---|
| 36 | C₂H₅ | C₂H₅ | —NH—CH(CH₃)₂ | Cl |
| 37 | C₂H₅ | —CH₂—CH(OCH₃)—CH₃ | —NH—cyclopentyl | Cl |
| 38 | CH₃ | —CH(CH₃)—CH₂—CH₃ | —NH—cyclopentyl | Cl |
| 39 | C₂H₅ | —CH₂—C₆H₅ | —NH—cyclopentyl | Cl |
| 40 | CH₃ | CH₂=CH—CH₂ | —NH—cyclopentyl | Cl |
| 41 | C₂H₅ | C₂H₅ | —NH—cyclohexyl | Cl |
| 42 | —(CH₂)₂— | | —NH—cyclohexyl | Cl |
| 43 | C₂H₅ | —CH₂—C₆H₅ | —NH—cyclohexyl | Cl |
| 44 | CH₃ | CH₃ | —NH—cyclohexyl | Cl |
| 45 | CH₃ | —CH(CH₃)₂ | —N(CH₃)—cyclohexyl | Cl |
| 46 | CH₃ | CH₃ | —N(CH₃)—cyclohexyl | Cl |
| 47 | C₂H₅ | —cyclohexyl | —N(CH₃)—cyclohexyl | Cl |
| 48 | CH₃ | CH₃ | —N(CH₃)₂ | Cl |
| 49 | C₂H₅ | —cyclohexyl | —N(CH₃)₂ | Cl |
| 50 | CH₂=CH—CH₂ | CH₂=CH—CH₂ | —N(CH₃)₂ | Cl |
| 51 | CH₃ | —CH(CH₃)—C₂H₅ | —N(CH₃)₂ | Cl |
| 52 | CH₃ | CH₃ | —N(CH₃)₂ | Cl |
| 53 | C₂H₅ | C₂H₅ | —N(C₂H₅)₂ | Cl |
| 54 | CH₃ | —cyclohexyl | —N(C₂H₅)₂ | Cl |

-continued

| | R¹ | R² | R³ | Y |
|---|---|---|---|---|
| 55 | CH₃ | CH₃ | —N⟨pyrrolidine⟩ | Cl |
| 56 | CH₃ | CH₂—CH(OCH₃)—CH₃ | —N⟨pyrrolidine⟩ | Cl |
| 57 | | —(CH₂)₂— | —N⟨pyrrolidine⟩ | Cl |
| 58 | CH₂=CH—CH₂ | CH=CH—CH₂ | —N⟨pyrrolidine⟩ | Cl |
| 59 | CH₃ | —cyclopentyl | —N⟨pyrrolidine⟩ | Cl |
| 60 | CH₃ | —CH—phenyl | —N⟨pyrrolidine⟩ | Cl |
| 61 | CH₃ | —CH(CH₃)—C₂H₅ | —N⟨pyrrolidine⟩ | Cl |
| 62 | CH₃ | —CH₂—CH(CH₃)₂ | —N⟨piperidine⟩ | Cl |
| 63 | C₂H₅ | —cyclohexyl (H) | —N⟨piperidine⟩ | Cl |
| 64 | CH₃ | —CH₂—CH(OCH₃)—CH₃ | —N⟨piperidine⟩ | Cl |
| 65 | C₂H₅ | C₂H₅ | —N⟨piperidine⟩ | Cl |
| 66 | C₂H₅ | —CH—phenyl | —N⟨piperidine⟩ | Cl |

The compounds of the invention are valuable medicaments and are distinguished by a very good diuretic and saluretic action.

Some patent specifications report on an anorectic, central nervous system stimulating and diuretic action of derivatives of 4-aryl-1,3-thiazolidine-4-ol (c.f. DOS 1,938,674, U.S. Pat. No. 3,671,534); these are compounds without sulfonamide groups at the aromatic nucleus and their diuretic action depends to a high degree on a specific substitution of the thiazolidine ring. It was surprising that, independent of this specific substituion at the ring, the novel compounds of the invention have a very strong salidiuretic action which is due to the introduction of a sulfonamide group into the 3-position of the benzene nucleus and which is distinctly superior qualitatively and quantitatively to that of the known thiazolidine derivatives. Moreover, the less desired anorectic and nervous system stimulating action component is largely suppressed.

The salidiuretic action of the compounds of the invention was determined on the rat with a unit dose of 50 mg/kg per os. It was found that this action was superior to the salidiuretic action of known commercial preparations of the thiazide group, for example the hydrochlorothiazide, and to that of chlorothalidone. In addition thereto, the novel compounds of the invention are distinguished by a long lasting action time which corresponds approximately to that of chlorothalidone. Therefore, the novel compounds of the invention are suitable in particular for the treatment of hypertonic conditions, in which case they will be combined with an antihypertonic agent as is usual today.

Therapeutic compositions of the novel compounds are in particular tablets, dragees, capsules, suppositories as well as solutions or suspensions in ampoules for parental administration (i.v., s.c. and i.m.). The products of the invention are contained in these compositions preferably in the form of their acid addition salts. The therapeutical dosage unit is between 5 and 500 mg. In addition to the usual filler and carrier substances, these compositions may also contain an antihypertensive agent, especially if they are intended for the therapy of high blood pressure, for example reserpin, hydralazine, guanethidine, α-methyldopa or clonidine.

Moreover, therapeutical combination compositions with potassium-retaining compounds such as aldosterone-antagonists, for example spironolactone, or pseudo-aldosterone-antagonists such as Triamterene or Amiloride are of interest. Furthermore, the K+ -substitution may also be made with the aid of various forms for administration, for example dragees, tablets, effervescent tablets, lotions, etc.

The following Examples illustrate the invention. In these examples, the melting and decomposition points are not corrected.

EXAMPLE 1

4-(3-Acetylsulfamoyl-4-chloro-phenyl)-3-methyl-2-methylimino-1,3-thiazolidine-4-ol-hydrobromide 10.5 g of 3'-acetylsulfamoyl-2-bromo-4'-chloro-acetophenone are dissolved in 100 ml of ethanol and heated to 45°–50° C during 5 minutes after the addition of 3 g of 1,3-dimethyl thiourea. After standing overnight at 20° C the solvent is expelled under reduced pressure, the residue is dissolved in acetone and the product is precipitated with diisopropyl ether while stirring.

Amorphous solid substance, decomposition point: beginning at 86° C.

EXAMPLE 2

4-(3-Acetylsulfamoyl-4-chloro-phenyl)-3-ethyl-2-isopropylimino-1,3-thiazolidine-4-ol-hydrobromide 3.7 g (0.01 mol) of 3'-acetylsulfamoyl-2-bromo-4'-chloroacetophenone and 1.5 g (0.01 mol) of 1-ethyl-3-isopropylthio urea are heated to 50° C during 3 to 5 minutes in 50 ml of acetone. The colorless crystals are filtered off after standing overnight. Melting point: 189° C (decomposition).

EXAMPLE 3

4-(4-Chloro-3-methylaminocarbonylsulfamoyl-phenyl)-3-methyl-2-methylimino-1,3-thiazolidine-4-ol-hydrobromide is obtained in a manner analogous to Example 2 from 2-bromo-4'-chloro-3'-methylaminocarbonylsulfamoyl-acetophenone and 1,3-dimethylthio urea.

Melting point: 188° C (decomposition).

EXAMPLE 4

3-Ethyl-2-ethylimino-4-(4-chloro-3-methylaminocarbonylsulfamoylphenyl)-1,3-thiazolidine-4-ol-hydrobromide is obtained in a manner analogous to Example 2 from 2-bromo-4'-chloro-3'-methylaminocarbonylsulfamoyl-acetophenone with 1,3-diethylthiourea.

Melting point: 185° C (decomposition).

EXAMPLE 5

3-Allyl-2-allylimino-4-(4-chloro-3-methylaminocarbonylsulfamoylphenyl-1,3-thiazolidine-4-ol-hydrobromide is obtained in a manner analogous to Example 2 from 2-bromo-4'-chloro-3'-methylamino-carbonylsulfamoyl-acetophenone with 1,3-diallylthiourea.

Melting point: 193° C (decomposition).

EXAMPLE 6

4-(3-n-Butylaminocarbonylsulfamoyl-4-chloro-phenyl)-3-methyl-2-methylimino-1,3-thiazolidine-4-ol-hydrobromide is obtained in a manner analogous to Example 2 from 2-bromo-3'-butylaminocarbonylsulfamoyl-4'-chloro-acetophenone and 1,3-dimethylthiourea.

Melting point: 147° C (decomposition).

EXAMPLE 7

4-(3-n-Butylaminocarbonylsulfamoyl-4-chloro-phenyl)-2-isopropylimino-3-methyl-1,3-thiazolidine-4-ol-hydrobromide is obtained in a manner analogous to Example 2 from 2-bromo-3'-n-butylaminocarbonylsulfamoyl-4'-chloro-acetophenone and 1-isopropyl-3-methyl-thiourea.

Melting point: 181° C (decomposition).

EXAMPLE 8

4-(4-Chloro-3-methoxycarbonylsulfamoyl-phenyl)-3-methyl-2-methylimino-1,3-thiazolidine-4-ol-hydrobromide is obtained in a manner analogous to Example 2 from 2-bromo-4'-chloro-3'-methoxycarbonylsulfamoyl-acetophenone with 1,3-dimethyl-thiourea and subsequent precipitation with 80 ml of diethyl ether.

Decomposition beginning at 103° C.

EXAMPLE 9

4-(3-Ethoxycarbonylsulfamoyl-4-chloro-phenyl)-3-methyl-2-methylimino-1,3-thiazolidine-4-ol-hydrobromide is obtained in a manner analogous to Example 8 from 3'-ethoxycarbonylsulfamoyl-2-bromo-4'-chloro-acetophenone and 1,3-dimethylthiourea.

Decomposition beginning at 132° C.

EXAMPLE 10

4-(3-Ethoxycarbonylsulfamoyl-4-chloro-phenyl)-2-isobutylimino-3-methyl-1,3-thiazolidine-4-ol-hydrobromide is obtained in a manner analogous to Example 8 from 3'-ethoxycarbonylsulfamoyl-2-bromo-4'-chloroacetophenone and 1-methyl-3-isobutyl-thiourea.

Melting point: 193° C (decomposition).

EXAMPLE 11

4-(4-Chloro-3-propionylsulfamoyl-phenyl)-3-methyl-2-methylimino-1,3-thiazolidine-4-ol-hydrobromide is obtained in a manner analogous to Example 2 from 2-bromo-4'-chloro-3'-propionylsulfamoyl-acetophenone and 1,3-dimethylthiourea, the solvent is decanted and the amorphous precipitate is crystallized under 50 ml of ethyl acetate. Decomposition beginning at 105° C.

EXAMPLE 12

4-(3-Acetylsulfamoyl-4-bromo-phenyl)-3-methyl-2-methylimino-1,3-thiazolidine-4-ol-hydrobromide is obtained in a manner analogous to Example 11 from 3'-acetylsulfamoyl-2,4'-dibromoacetophenone and 1,3-dimethylthiourea.

Melting point: 201° C (decomposition).

EXAMPLE 13

4-(3-Acetylsulfamoyl-4-bromo-phenyl)-3-ethyl-2-cyclohexylimino-1,3-thiazolidine-4-ol-hydrobromide is obtained in a manner analogous to Example 8 from 3'-acetylsulfamoyl-2,4'-dibromo-acetophenone and 1-ethyl-3-cyclohexylthiourea and the amorphous product is crystallized with 50 ml of ethyl acetate heated to 35° to 40° C.

Melting point: 155°–158° C (decomposition).

EXAMPLE 14

4-(3-Acetylsulfamoyl-4-chloro-phenyl)-2-cyclohexylimino-3-methyl-1,3-thiazolidine-4-ol-hydrobromide is obtained in a manner analogous to Example 2 from 3'-acetylsulfamoyl-2-bromo-4'-chloro-acetophenone and 1-methyl-3-cyclohexyl-thiourea, the product is precipitated with 50 ml of ethyl acetate and the amorphous body is solidified by trituration with a little ether.

Decomposition beginning at 72° C.

EXAMPLE 15

4-(3-Acetylsulfamoyl-4-chloro-phenyl)-3-allyl-2-allylimino-1,3-thiazolidine-4-ol-hydrobromide is obtained in a manner analogous to Example 2 from 3'-acetylsulfamoyl-2-bromo-4'-chloroacetophenone and 1,3-diallylthiourea, the product is precipitated with 80 ml of ether, the solvent is decanted, the amorphous residue is dissolved in 70 ml of water and lyophilized.

Amorphous acid substance, decomposition beginning at 120° C.

EXAMPLE 16

3-(3-Acetylsulfamoyl-4-chloro-phenyl)-3-hydroxy-2,3,5,6-tetrahydroimidazo[2,1-b]thiazole-hydrobromide is obtained in a manner analogous to Example 15 from 3'-acetylsulfamoyl-2-bromo-4'-chloroacetophenone and finely ground 2-imidazolidine-thione.

Amorphous solid body, decomposition beginning at 110° C.

EXAMPLE 17

4-(3-Acetylsulfamoyl-4-chloro-phenyl)-2-benzylimino-3-methyl-1,3-thiazolidine-4-ol-hydrobromide is obtained in a manner analogous to Example 14 from 3'-acetylsulfamoyl-2-bromo-4'-chloro-acetophenone and 1-benzyl-3-methyl-thiourea.

Amorphous solid substances, decomposition starting at 90° C.

EXAMPLE 18

4-(3-Acetylsulfamoyl-4-bromo-phenyl)-3-n-propyl-2-n-propylimino-1,3-thiazolidine-4-ol-hydrobromide is obtained in a manner analogous to Example 2, with subsequent precipitation of the product with diisopropyl ether, from 3'-acetylsulfamoyl-2,4'-dibromo-acetophenone and 1,3-di-n-propylthiourea.

Amorphous solid substance, decomposition starting at 125° C.

EXAMPLE 19

4-(4-Chloro-3-cyclohexylaminocarbonylsulfamoyl-phenyl)-3-methyl-2-methylimino-1,3-thiazolidine-4-ol-hydrobromide is obtained in a manner analogous to Example 18 from 2-bromo-4'-chloro-3'-cyclohexylamino-carbonylsulfamoyl-acetophenone and 1,3-dimethylthiourea. The amorphous precipitate is solidified under ethyl acetate.

Amorphous solid substance, decomposition starting at 81° C.

EXAMPLE 20

3-Allyl-2-allylimino-4-(4-chloro-3-cyclohexylaminocarbonylsulfamoyl-phenyl)-1,3-thiazolidine-4-ol-hydrobromide is obtained in a manner analogous to Example 19 from 2-bromo-4'-chloro-3'-cyclohexylamino-carbonylsulfamoyl-acetophenone and 1,3-diallylthiourea.

Amorphous solid substance, decomposition starting at 101° C.

EXAMPLE 21

3-Ethyl-4-(4-chloro-3-cyclohexylaminocarbonylsulfamoyl-phenyl)-2-isobutylimino-1,3-thiazolidine-4-ol-hydrobromide is obtained in a manner analogous to Example 19 from 2-bromo-4'-chloro-3'-cyclohexylamino-carbonylsulfamoyl-acetophenone and 1-ethyl-3-isobutyl-thiourea.

Melting point: 156° C (decomposition).

EXAMPLE 22

3-(3-Acetylsulfamoyl-4-bromo-phenyl)-3-hydroxy-2,3,5,6-tetrahydroimidazo[2,1-b]thiazole-hydrobromide 4.1 g (0.01 mol) of 3'-acetyl-2,4'-dibromoacetophenone are heated in 40 ml of methanol with 1g (0.01mol) of 2-thiazolidinethione during 10 minutes to 45°–50° C, the mixture is allowed to stand at 20° C during 10 hours and then introduced dropwise into 100 ml of thoroughly stirred ethyl acetate. The amorphous precipitate is crystallized under 40 ml of warm ethyl acetate.

Melting point: 193° C (decomposition).

EXAMPLE 23

4-(3-Acetylsulfamoyl-4-chloro-phenyl)-3-ethyl-2-(2-methoxypropylimino)-1,3-thiazolidine-4ol-hydrobromide 3.7 g (0.01 mol) of 3'-acetylsulfamoyl-2-bromo-4'-chloroacetophenone are stirred at 20° C during 24 hours in 20 ml of ethyl acetate with 1.8 g (1.01 mol) of 1-ethyl-3-(2-methoxypropyl)thiourea, 60 ml of ether are added and the amorphous oily precipitate is solidified by trituration after under 40 ml of ether decanting the solvent. Amorphous solid substance capable of flowing, decomposition starting at 65° C.

EXAMPLE 24

4-(3-Acetylsulfamoyl-4-chloro-phenyl)-3-methyl-2-(2-phenyl-ethylamino)-1,3-thiazolidine-4-ol-hydrobromide is obtained in a manner analogous to Example 23 from 3'-acetylsulfamoyl-2-bromo-4'-chloro-acetophenone and 1-methyl-3-(2-phenylethyl)-thiourea.

Amorphous solid substance, decomposition starting at 105° C.

EXAMPLE 25

4-(3-Acetylsulfamoyl-4-chloro-phenyl)-3-n-propyl-2-n-propylimino-1,3-thiazolidine-4-ol-hydrobromide is obtained in a manner analogous to Example 23 from 3'-acetylsulfamoyl-2-bromo-4'-chloro-acetophenone and 1,3-di-n-propyl-thiourea.

Amorphous solid substance, decomposition starting at 83° C.

EXAMPLE 26

3-(3-Acetylsulfamoyl-4-chloro-phenyl)-3-hydroxy-2,3,6,7-tetrahydro-5H-thiazolo[3,2-a]pyrimidine-hydrochloride is obtained in a manner analogous to Example 22 from 3'-acetylsulfamoyl-2-bromo-4'-chloroacetophenone and ground 3,4,5,6-tetrahydro-2-pyrimidinthiol.

Amorphous solid substance, decomposition starting at 106° C.

EXAMPLE 27

4-(3-Acetylsulfamoyl-4-chloro-phenyl)-3-methyl-2-methylimino-1,3-thiazolidine- 4-ol-hydrochloride Method A 9.2 g (0.02 mol) of 4-(3-acetylsulfamoyl-4-chloro-phenyl)-3-methyl-2-methylimino-1,3-thiazolidine-4-ol-hydrobromide are dissolved in 80 ml of water, superimposed by 20 ml of ethyl acetate, whereupon a glass electrode being immersed indicated pH 4.2. Saturated NaHCO$_3$-solution is added dropwise with thorough stirring until pH 4.3 is reached, the organic phase is separated in a separating funnel and the extraction is repeated at pH 4.4, pH 4.5, pH 4.6, pH 4.8, pH 5.0, pH 5.3 and pH 5.6. The combined organic extraction fractions are dried over magnesium sulfate and the solution is condensed to a volume of about 30 ml under reduced pressure. The acid pH is adjusted with ethereal HCl-solution. After decanting the solvent, the residue is solidified under ethyl acetate.

Amorphous solid substance, decomposition starting at 135° C.

Method B (a) 6.8 g (0.02 mol) of 4-(4-chloro-3-sulfamoyl-phenyl)-3-methyl-2-methylimino-1,3-thiazolidine-4-ol (melting point: 187° C, decomposition) are introduced with the exclusion of atmospheric moisture into a stirred solution of 0.46 g of sodium in 80 ml of anhydrous methanol, heated to 40° C during 15 minutes and stirred again at 20° C for 3 hours. The solvent is condensed to a volume of about 30 ml with the exclusion of atmospheric moisture and under reduced pressure and the sodium sulfamidate of the starting substance is obtained by adding 50 ml of anhydrous ether in quantitative yield.

(b) The salt prepared under method (a) is suspended in 250 ml of anhydrous dioxane and thoroughly stirred at 20° C during 40 hours after the addition 2.1 g of acetic anhydride. The solvent is expelled under reduced pressure, the residue is taken up with 30 ml of methanol and the acid pH range is adjusted with methanolic hydrochlorid acid. After distilling off 10 ml of solvent under reduced pressure the mixture is allowed to stand at room temperature during 24 hours, the precipitated sodium chloride is centrifuged off and the desired product is precipitated with 40 ml of ether. Amorphous solid substance, decomposition at 130°–133° C.

Method C prepared from 3'-acetylsulfamoyl-2,4'-dichloroacetophenone and 1,3-dimethylthiourea in a manner analogous to Example 13.

Amorphous solid substance, decomposition at 137° C.

EXAMPLE 29

4-(3-Acetylsulfamoyl-4-chloro-phenyl)-3-ethyl-2-isopropylimino-1,3-thiazolidine-4-ol-hydrochloride is obtained according to Method A in a manner analogous to Example 27/A from 4-(3-Acetylsulfamoyl-4-chloro-phenyl)-3-ethyl-2-isopropylimino-1,3-thiazolidine-4-ol-hydrobromide.

Amorphous solid substance, decomposition starting at 77° C.

Method B: in a manner analogous to Example 27/B from 3-ethyl-4-(4-chloro-3-sulfamoylphenyl)-2-isopropylimino-1,3-thiazolidine-4-ol (melting point: 175° C, decomposition) with acetic anhydride and methanolic hydrochloric acid.

Amorphous solid substance, decomposition starting at 71° C.

EXAMPLE 29

4-(4-Chloro-3-methylaminocarbonylsulfamoyl-phenyl)-3-methyl-2-methylimino-1,3-thiazolidine-4-ol-hydrobromide is obtained in a manner analogous to Example 27/B from 4-(4-chloro-3-sulfamoyl-phenyl)-3-methyl-2-methylimino-1,3-thiazolidine-4-ol with methylisocyanate as acylating agent.

Melting point: 185°–187° C (decomposition).

EXAMPLE 30

4-(4-Chloro-3-cyclopentylaminocarbonylsulfamoyl-phenyl)-3-methyl-2-methylimino-1,3-thiazolidine-4-ol-hydrobromide is obtained in a manner analogous to Example 2 from 2-bromo-4'-chloro-3'-cyclopentylaminocarbonylsulfamoyl-acetophenone and 1,3-dimethylthiourea.

Melting point: 185° C (decomposition).

EXAMPLE 31

2-Benzylimino-4-(4-chloro-3-cyclopentylaminocarbonylsulfamoylphenyl)-3-methyl-1,3-thiazolidine-4-ol-hydrobromide is obtained in a manner analogous to Example 23 from 2-bromo-4'-chloro-3'-cyclopentylamino-carbonylsulfamoylacetophenone and 1-methyl-3-benzyl-thiourea.

Melting point: 165° C (decomposition).

EXAMPLE 32

3-(4-Chloro-3-cyclopentylaminocarbonylsulfamoyl-phenyl)-3-hydroxy-2,3,6,7-tetrahydro-5H-thiazolo[3,2-a]pyrimidinehydrobromide is obtained in a manner analogous to Example 22 from 2-bromo-4'-chloro-3'-cyclopentylamino-carbonylsulfamoylacetophenone and 3,4,5,6-tetrahydro-2-pyrimidinethiol.

Melting point: 188° C (decomposition).

EXAMPLE 33

4-(4-Chloro-3-di-n-propylaminocarbonylsulfamoyl-phenyl)-3-methyl-2-methylimino-1,3-thiazolidine-4-ol-hydrobromide is obtained in a manner analogous to Example 13 from 2-bromo-4'-chloro-3'-di-n-propylaminocarbonylsulfamoylacetophenone and 1,3-dimethylthiourea.

Melting point: 203° C (decomposition).

EXAMPLE 34

2-Benzylimino-4-[4-chloro-3-(1-piperidylcarbonylsulfamoyl)phenyl]-3-methyl-1,3-thiazolidine-4-ol-hydrobromide is obtained in a manner analogous to Example 23 from 2-bromo-4'-chloro-3'-(1-piperidylcarbonyl-sulfamoyl)-acetophenone and 1-methyl-3-benzyl-thiourea.

Amorphous solid substance, decomposition starting at 128° C.

Preparation of the Preliminary Products

I. Halogenated ketones of the general formula II

I.1. By bromination

3'-Acetylsulfamoyl-2-bromo-4'-chloro-acetophenone:

5.5 g (0.02 mol) of 3'-acetylsulfamoyl-4'-chloroacetophenone are heated to boiling under reflux in 30 ml of ethyl acetate to which 2 ml of a solution of 3.2 g (0.02 mol) of bromine in 8 ml of ethyl acetate are added dropwise. Boiling is continued until the bromine color in the reaction mixture has suddenly disappeared, the solution is cooled to 45° to 35° C and the residual mixture of bromine and ethyl acetate is rapidly added dropwise with stirring. The solution is stirred during 30 minutes at room temperature and the solvent is distilled off.

Melting point: 150° C (from a small amount of isopropanol). The 2-bromo-acetophenones (Z = Br) listed in Table 1 of the general formula II are obtained in an analogous manner:

| $R^3$ | Y | Melting point |
|---|---|---|
| $C_2H_5$ | Cl | 146° C decomposition |
| $CH_3-O-$ | Cl | 118° C decomposition |
| $C_2H_5-O-$ | Cl | 131° C decomposition |
| $CH_3-NH-$ | Cl | 152° C decomposition |
| $n-C_4H_9-NH$ | Cl | 109° C decomposition |
|  | Cl | 112° C decomposition |
| 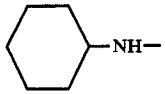 | Cl | 135° C decomposition |
| 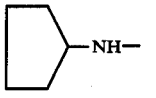 | Cl | 170° C decomposition from acetonitrile |
| $(n-C_3H_7)_2N-$ | Cl | 178° C decomposition from ether/ethyl acetate) |

I.2. By acylation

3'-Acetylsulfamoyl-2,4'-dibromo-acetophenone:

18.8 g (0.05 mol) of 2,4-dibromo-3'-sulfamoyl-acetophenone are boiled under reflux during 1¼ hour in about 100 ml of acetic anhydride, the reaction mixture is cooled and the desired product is precipitated with 600 ml of diisopropyl ether and 400 ml of petroleum ether.

Melting point: 164° C.

From 2,4'-dichloro-3'-sulfamoyl-acetophenone, 3'-acetylsulfamoyl-2,4'-dichloro-acetophenone (melting point: 177° C) is obtained in an analogous manner.

II. 3'-acylsulfamoyl-acetophenones of the general formula XI as preliminary products of the halogenated ketones II are prepared as follows:

II.1. In a manner analogous to I.2.

from 4'-chloro-3'-sulfamoyl-acetophenone with acetic anhydride, 3'-acetylsulfamoyl-4'-chloroacetophenone (melting point: 155° C) and, with propionic acid anhydride, 4'-chloro-3'-propionyl-sulfamoyl-acetophenone (melting point: 130° C).

II.2.

(a) 23.4 g (0.1 mol) of 4'-chloro-3'-sulfamoyl-acetophenone are cooled to 0°–5° C after dissolution in 600 ml of acetone and 50 ml of 2N sodium hydroxide solution and 6.5 g of methylisocyanate are added dropwise at that temperature. The solution is stirred for another 4 hours at room temperature, one and a half liters of water are added, the pH is adjusted to 1 to 2 with hydrochloric acid, the acetone is distilled off and the crystalline 4'-chloro-3'-methylaminocarbonyl-sulfamoyl-acetophenone is filtered off (melting point: 154° C).

(b) In a corresponding reaction with 14 g of cyclohexylisocyanate, 4'-chloro-3'-cyclohexylaminocarbonylsulfamoyl-acetophenone is obtained which melts at 172° C.

II.3.

(a). 23.4 g (0.1 mol) of 4'-chloro-3'-sulfamoyl-acetophenone are boiled under reflux for 5 hours in 200 ml of anhydrous dioxane with 27.6 g of ground, anhydrous potassium carbonate and heated to boiling during a further 5 hours after adding 7.8 ml of chloroformic acid methyl ester. The solvent is expelled, the residue is dissolved in water and the pH is adjusted to 1–2 with 2 N hydrochloric acid. The amorphous precipitated 4'-chloro-3'-methoxycarbonylsulfamoyl-acetophenone is completely crystallized after standing for a short time.

(Melting point: 164° C (decomposition)).

(b) In a corresponding reaction with 9.6 ml of chloroformic acid ethyl ester, 3'-ethoxycarbonylsulfamoyl-4'-chloro-acetophenone is obtained.

Melting point: 106° C.

II.4

(a) 29.1 g (0.1 mol) of 4'-chloro-3'-methoxycarbonalsulfamoylacetophenone are heated to 100° C for 6 hours in an autoclave with 7.3 g (0.1 mol) of n-butylamine in 100 ml of dioxane. The solvent is expelled, 300 ml of water are added to the residue, the pH is adjusted to 1–2 with 2 N hydrochloric acid and the crystalline 3'-n-butylaminocarbonylsulfamoyl-4'-chloroacetophenone is filtered off after standing for several hours.

Melting point: 153° C, decomposition (from methanol-water). In a manner analogous to II.4 a), 4'-chloro-3'-methoxycarbonylsulfamoyl-acetophenone yields (b) with cyclopentylamine, 4'-chloro-3'-cyclopentylaminocarbonyl-sulfamoyl-acetophenone (melting point: 168° C)

(c) with piperidine, 4'-chloro-3'-pentamethyleneamino-carbonylsulfamoyl-acetophenone in the form of an amorphous oil which is further processed in this form (d) with di-n-propylamine, 4'-chloro-3'-di-n-propylaminocarbonyl-sulfamoyl-acetophenone as amorphous oil which is further processed in this form.

What is claimed is:

1. A thiazolidine compound of the formula

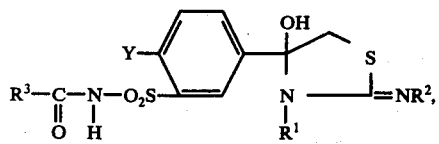

and physiologically tolerated salts thereof, wherein $R^1$ taken alone is alkyl or alkenyl having 1 to 4 carbon atoms; $R^2$ taken alone is alkyl or alkenyl having 1 to 6 carbon atoms which may be substituted by alkoxy having 1 to 2 carbon atoms, by cycloalkyl having 3 to 8 carbon atoms, or by phenylalkyl having 1 or 2 carbon atoms in the alkyl; $R^1$ and $R^2$ taken together are 1,2-ethylene or 1,3-propylene; $R^3$ is hydrogen, lower alkyl, or alkoxy having 1 to 3 carbon atoms, or is —$NR^4R^5$ in which $R^4$ and $R^5$ taken alone are identical or different and each is hydrogen or lower alkyl having 1 to 4 carbon atoms, and if $R^5$ is hydrogen then $R^4$ may also by cycloalkyl having 5 to 8 carbon atoms, or in which $R^4$ and $R^5$ taken together with the nitrogen atom to which they are attached are pyrrolidine or piperidine; and Y is chlorine or bromine.

2. A compound as claimed in claim 1, which is 4-(3-acetylsulfamoyl-4-chloro-phenyl)-3-methyl-2-methylimino-1,3-thiazolidine-4-ol-hydrobromide.

3. A compound as claimed in claim 1, which is 4-(4-chloro-3-methylaminocarbonylsulfamoyl-phenyl)-3-methyl-2-methylamino-1,3-thiazolidine-4-ol-hydrobromide.

4. A compound as claimed in claim 1, which is 4-(4-chloro-3-methoxycarbonylsulfamoyl-phenyl)-3-methyl-2-methylimino-1,3-thiazolidine-4-ol-hydrobromide.

5. A compound as claimed in claim 1, which is 4-(4-chloro-3-cyclohexylaminosulfamoyl-phenyl)-3-methyl-2-methylimino-1,3-thiazolidine-4-ol-hydrobromide.

6. A pharmaceutical composition for inducing salidiuresis, said composition comprising a salidiuretically effective amount of a compound or salt as claimed in claim 1 in combination with a pharmaceutically acceptable carrier.

7. A pharmaceutical composition as claimed in claim 6 comprising from 10 to 100 mg of said compound or salt.

8. A method for inducing salidiuresis in a patient which method comprises administering to said patient, orally, parenterally, or in suppository form, a salidiuretically effective amount of a compound as claimed in claim 1.

* * * * *